US007829757B2

(12) United States Patent
Habu et al.

(10) Patent No.: US 7,829,757 B2
(45) Date of Patent: Nov. 9, 2010

(54) SGRF GENE-MODIFIED MOUSE

(75) Inventors: Kiyoshi Habu, Shizuoka (JP); Yuichi Hirata, Ibaraki (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/499,694

(22) Filed: Jul. 8, 2009

(65) Prior Publication Data

US 2009/0288177 A1 Nov. 19, 2009

Related U.S. Application Data

(63) Continuation of application No. 10/493,526, filed as application No. PCT/JP02/11047 on Oct. 24, 2002, now abandoned.

(30) Foreign Application Priority Data

Oct. 24, 2001 (JP) ............................. 2001-326858

(51) Int. Cl.
*G01N 33/00* (2006.01)
(52) U.S. Cl. ............................................ 800/3; 800/18
(58) Field of Classification Search .................. None
See application file for complete search history.

(56) References Cited

U.S. PATENT DOCUMENTS

| 6,610,285 B1 | 8/2003 | Hirata |
| 2004/0258686 A1 | 12/2004 | Chirica et al. |

FOREIGN PATENT DOCUMENTS

| EP | 1 072 610 | 1/2001 |
| WO | WO 99/54357 | 10/1999 |
| WO | WO 02/33054 | 4/2002 |

OTHER PUBLICATIONS

Brombacher et al., "IL-12 is dispensable for innate and adaptive immunity against low doses of Listeria monocytogenes," International Immunology 11(3):325-332 (1999).
Capecchi, "The new mouse genetics: Altering the genome by gene targeting," Trends in Genetics, 5(3):70-76 (1989).
Cytokines / Zousyoku Inshi, Jikken Igaku Bessatsu Bio Science Yougo Library, 1998; Revised edition: 86-7. (English translation attached).
Decken et al. "Interleukin-12 is essential for a protective Th1 response in mice infected with Cryptococcus neoformans," Infection and Immunity 66(10):4994-5000 (1998).
Lariviere et al., "Transgenic Studies of Pain and Analgesia: Mutation or Background Genotype?" J. Pharm. And Exp. Therap. 297:467-473 (2001).
Leonard et al., "Prevention of Experimental Autoimmune Encephalomyelitis by Antibodies Against Interleukin 12," J. Exp. Med. 181(1):381-386 (1995).
Magram et al., "IL-12-Deficient Mice Are Defective in IFNγ Production and Type 1 Cytokine Responses," Immunity 4(5):471-481 (1996).
Moreadith et al., "Gene targeting in embryonic stem cells: the new physiology and metabolism," J. Mol. Med. 75:208-216 (1997).
Mullins et al., "Perspectives Series: Molecular Medicine in Genetically Engineered Animals," J. Clin. Invest. 98:S37-S40 (1996).
Oppmann et al., "Novel p19 Protein Engages IL-12p40 to Form a Cytokine, IL-23, with Biological Activities Similar as Well as Distinct from IL-12," Immunity 13(5):715-725 (2000).
Seamark, "Progress and Emerging Problems in Livestock Transgenesis: a Summary Perspective," Reprod. Fertil. Dev. 6:653-657 (1994).
Segal et al., "An Interleukin (IL)-10/IL-12 Immunoregulatory Circuit Controls Susceptibility to Autoimmune Disease," The Journal of Experimental Medicine 187(4):537-546 (1998).
Sigmund, "Viewpoint: Are Studies in Genetically Altered Mice Out of Control?" Arterioscler. Thromb. Vasc. Biol., pp. 1425-1429 (2000).
Takai et al., "FcR gamma chain deletion results in pleiotrophic effector cell defects," Cell 76(3):519-529 (1994).
Wakeham et al., "Lack of both types 1 and 2 cytokines, tissue inflammatory responses, and immune protection during pulmonary infection by *Mycobacterium bovis* Bacilli Calmete-Guerin in IL-12-deficient mice," The Journal of Immunology 160:6101-6111 (1998).
Wiekowski et al. "Ubiquitous transgenic expression of the IL-23 subunit p19 induces multiorgan inflammation, runting, infertility, and premature death," The Journal of Immunology 166:7563-7570 (2001).
Fish & Richardson P.C., Preliminary Amendment, in U.S. Appl. No. 10/493,526, filed Apr. 22, 2004 (7 pages).
Restriction Requirement, in U.S. Appl. No. 10/493,526, mailed Nov. 3, 2005 (6 pages).
Fish & Richardson P.C., Response to Restriction Requirement, in U.S. Serial No. 10/493,526, mailed Nov. 3, 2005, filed Apr. 28, 2006 (6 pages).
Office Action, in U.S. Appl. No. 10/493,526, mailed May 22, 2006, (12 pages).
Fish & Richardson P.C., Response to Office Action, in U.S. Appl. No. 10/493,526, mailed May 22, 2006, filed Nov. 21, 2006 (7 pages).

(Continued)

*Primary Examiner*—Anne-Marie Falk
(74) *Attorney, Agent, or Firm*—Fish & Richardson P.C.

(57) ABSTRACT

A targeting vector was constructed by replacing exon regions in the SGRF gene with appropriate drug marker genes. This vector was transfected into mouse ES cell lines to obtain chimeric mice, which were then crossed with C57BL/6J mice to obtain mice comprising cells in which one SGRF gene alleles was inactivated. By crossing these mice with each other, the present inventors succeeded in producing mice in which both SGRF gene alleles were inactivated. These genetically modified animals can be used to predict the side effects of drugs such as SGRF antagonists.

11 Claims, 6 Drawing Sheets

OTHER PUBLICATIONS

Office Action, in U.S. Appl. No. 10/493,526, mailed Feb. 26, 2007 (9 pages).

Fish & Richardson P.C., Response to Office Action, in U.S. Appl. No. 10/493,526, mailed Feb. 26, 2007, filed Aug. 27, 2007 (8 pages).

Office Action, in U.S. Appl. No. 10/493,526, mailed Nov. 16, 2007 (15 pages).

Fish & Richardson P.C., Response to Office Action, in U.S. Appl. No. 10/493,526, mailed Nov. 16, 2007, filed Mar. 14, 2008 (8 pages).

Office Action, in U.S. Appl. No. 10/493,526, mailed Jul. 3, 2008 (10 pages).

Fish & Richardson P.C., Request for Continued Examination and Amendment in Reply to Final Office Action, in U.S. Appl. No. 10/493,526, filed Jan. 2, 2009 (8 pages).

Notice of Allowance, in U.S. Appl. No. 10/493,526, mailed Apr. 9, 2009 (8 pages).

EXON1 (SEQ ID NO: 1)

<u>AGATCT</u>GAGAAGCAGGGAACAAG<u>ATG</u>CTGGATTGCAGAGCAGTAATAATGCTATGGCTG

<u>Bgl</u>II SITE   TRANSLATIONAL INITIATION POINT →

TTGCCCTGGGTCACTCAGGGCCTGGCTGTGCCTAGGAGTAGCAGTCCTGACTGGGCTC

AGTGCCAGCAGCTCTCTCGGAATCTCTGCATGCTAGCCTGGAACGCACATGCACCAGC

GGGACATATG

INTRON1 (SEQ ID NO: 2)

GTAAGTGTCAGCTCCTGGGACCGCGCAGAAAACCTTCCCAGTCCTCCAAGTGTGTAGG

TTTAATGGAAGCTGTGGCCCCGGGTGGATCTGGAGGGTTGGAAGCCATCGTGGAATGA

GATAGGACAGAAGACTGGGGCTTCTGGAAGAGTTGTGGGCCGGCGGTTGAGCGGAAT

GCAAAGCGGTCACCTCGCCTCACTGTTCCCACTCCCTCCATTACAG

EXON2 (SEQ ID NO: 3)

AATCTACTAAGAGAAGAAGAGGATGAAGAGACTAAAAATAATGTGCCCCGTATCCAGTG

TGAAGATGGTTGTGACCCACAAGGACTCAAGGACAACAGCCAG

INTRON2 (SEQ ID NO: 4)

GTACCA*CTAAGCCGATGTTGATGTGTC*TAGGAGAGGGAGGTGAGAGGAAGCTGAGCGT

CCATGGCCATTTAGCTTTGTCTGAGATGACGAGGAGCCATAGTTGGCTTGAAGCCAGCC

TGAGCTGTGGGTGGTAAGTTTAAGGCCAAAGCCTAAGGTAGTGAAATGCTGTCTAAAGA

AAGAAAAAGGAAAAACAGAGGAAGGAAGAAAGGCAGGCAGGCACTAGGAAAGAGGAT

CTATCTGTCTTGATTGTTTTCTTCTTTCCCAG

FIG. 1

EXON3 (SEQ ID NO: 5)

TTCTGCTTGCAAAGGATCCGCCAAGGTCTGGCTTTTTATAAGCACCTGCTTGACTCTGA
CATCTTCAAAGGGGAGCCTGCTCTACTCCCTGATAGCCCCATGGAGCAACTTCACACCT
CCCTACTAGGACTCAGCCAACTCCTC

INTRON3 (SEQ ID NO: 6)

CAGGTATGAACTAGGGATCTGGAAGATAGGGCTAGCCAGTGTTTGAAAAAGAAGCTCG
GAGCTTAGTATCTGGAGTCCTTTCTGACTGTGTCCTGTGTCTTT

EXON4 (SEQ ID NO: 7)

CAGCCAGAGGATCACCCCCGGGAGACCCAACAGATGCCCAGCCTGAGTTCTAGTCAGC
AGTGGCAGCGCCCCCTTCTCCGTTCCAAGATCCTTCGAAGCCTCCAGGCCTTTTTGGCC
ATAGCTGCCCGGGTCTTTGCCCACGGAGCAGCAACTCTGACTGAGCCCTTAGTGCCAA
CAGCTTAAGGATGCCCAGGTTCCCATGGCTACCATGATAAGACTAATCTATCAGCCCAG
ACATCTACCAGTTAATTAACCCATTAGGACTTGTGCTGTTCTTGTTTCGTTTGTTTTGCG
TGAAGGGCAAGGACACCATTATTAAAGAGAAAAGAAACAAACCCCAGAGCAGGCAGCT
GGCTAGAGAAAGGAGCTGGAGAAGAAGAATAAAGT<u>CTCGAG</u>CCCTTGGCCTTGGAAGC
                                                                    *Xho* I SITE

GGGCAAGCAGCTGCGTGGCCTGAGGGGAAGGGGGCGGTGGCATCGAGAAACTGTGAG
AAAACCCAGAGCATCAGAAAAAGTGAGCCCAGGCTTTGGCCATTATCTGTAAGAAAAAC
AAGAAAAGGGGAACATTATACTTTCCTGGGTGGCTCAGGGAAATGT*GCAGATGCACAGT*
*ACTCCAGACAGC*AGCTCTGTACCTGCCTGCTCTGTCCCTCAGTTCTAACAGAATCTAGT
CACTAAGAACTAACAGGACTACCAATACGAACTGACAAATACTACCACTATGACCTGTG
ACAAAGCTGTTTATTTATTAAGTGGGAAGGGAACTTTTGATATTATTTATCCTTGTAACA
GTATAGATGATGGTTATTTATTCTATTTATAAGGAATTATGTATTTTTTTTTC*AATAAA*GAT
                                                                   mSGRF polyA
                                                               ADDITIONAL SIGNAL

TTATTTATGTGGCTCTCTGGGTCTAAATTTCTAAGTGTAGTCGGGAGAGAAAAGAGATG

FIG. 2

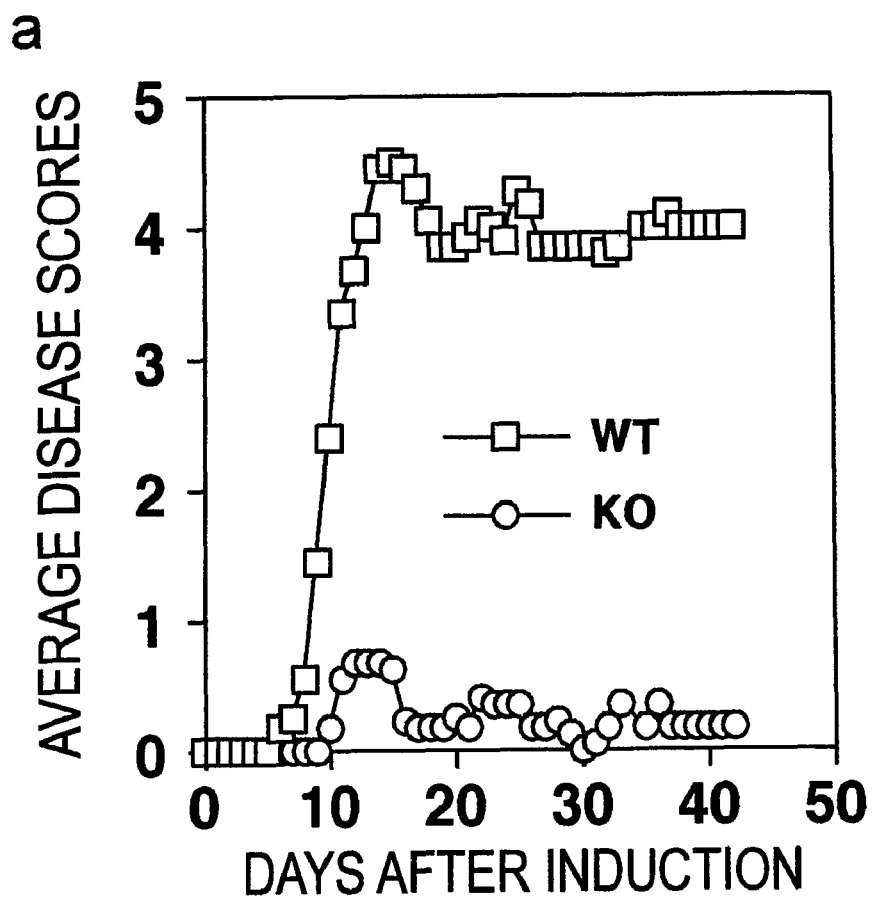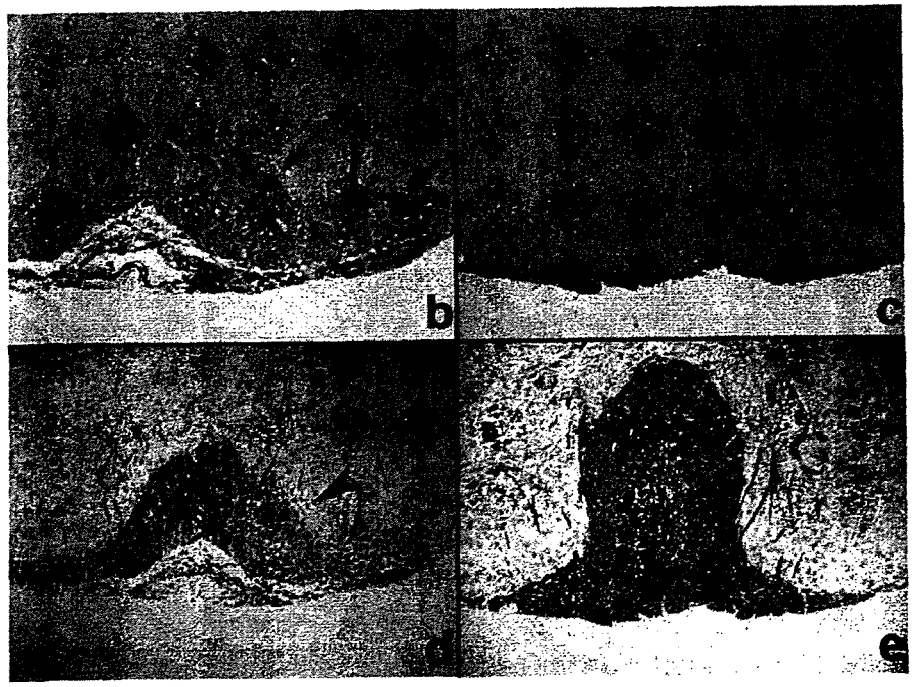
FIG. 6

```
                         SEQUENCE LISTING

<160> NUMBER OF SEQ ID NOS: 15

<210> SEQ ID NO 1
<211> LENGTH: 185
<212> TYPE: DNA
<213> ORGANISM: Mus musculus

<400> SEQUENCE: 1
agatctgaga agcagggaac aagatgctgg attgcagagc agtaataatg ctatggctgt      60
tgccctgggt cactcagggc ctggctgtgc ctaggagtag cagtcctgac tgggctcagt     120
gccagcagct ctctcggaat ctctgcatgc tagcctggaa cgcacatgca ccagcgggac     180
atatg                                                                185

<210> SEQ ID NO 2
<211> LENGTH: 219
<212> TYPE: DNA
<213> ORGANISM: Mus musculus

<400> SEQUENCE: 2
gtaagtgtca gctcctggga ccgcgcagaa aaccttccca gtcctccaag tgtgtaggtt      60
taatggaagc tgtggccccg ggtggatctg gagggttgga agccatcgtg gaatgagata     120
ggacagaaga ctggggcttc tggaagagtt gtgggccggc ggttgagcgg aatgcaaagc     180
ggtcacctcg cctcactgtt cccactccct ccattacag                            219

<210> SEQ ID NO 3
<211> LENGTH: 219
<212> TYPE: DNA
<213> ORGANISM: Mus musculus

<400> SEQUENCE: 3
gtaagtgtca gctcctggga ccgcgcagaa aaccttccca gtcctccaag tgtgtaggtt      60
taatggaagc tgtggccccg ggtggatctg gagggttgga agccatcgtg gaatgagata     120
ggacagaaga ctggggcttc tggaagagtt gtgggccggc ggttgagcgg aatgcaaagc     180
ggtcacctcg cctcactgtt cccactccct ccattacag                            219

<210> SEQ ID NO 4
<211> LENGTH: 265
<212> TYPE: DNA
<213> ORGANISM: Mus musculus

<400> SEQUENCE: 4
gtaccactaa gccgatgttg atgtgtctag gagagggagg tgagaggaag ctgagcgtcc      60
atggccattt agctttgtct gagatgacga ggagccatag ttggcttgaa gccagcctga     120
```

```
gctgtgggtg gtaagtttaa ggccaaagcc taaggtagtg aaatgctgtc taaagaaaga    180
aaaaggaaaa acagaggaag gaagaaaggc aggcaggcac taggaaagag gatctatctg    240
tcttgattgt tttcttcttt cccag                                         265

<210> SEQ ID NO 5
<211> LENGTH: 144
<212> TYPE: DNA
<213> ORGANISM: Mus musculus

<400> SEQUENCE: 5
ttctgcttgc aaaggatccg ccaaggtctg gcttttata agcacctgct tgactctgac     60
atcttcaaag gggagcctgc tctactccct gatagcccca tggagcaact tcacacctcc    120
ctactaggac tcagccaact cctc                                          144

<210> SEQ ID NO 6
<211> LENGTH: 102
<212> TYPE: DNA
<213> ORGANISM: Mus musculus

<400> SEQUENCE: 6
caggtatgaa ctagggatct ggaagatagg gctagccagt gtttgaaaaa gaagctcgga     60
gcttagtatc tggagtcctt tctgactgtg tcctgtgtct tt                      102

<210> SEQ ID NO 7
<211> LENGTH: 884
<212> TYPE: DNA
<213> ORGANISM: Mus musculus

<400> SEQUENCE: 7
cagccagagg atcacccccg ggagacccaa cagatgccca gcctgagttc tagtcagcag     60
tggcagcgcc cccttctccg ttccaagatc cttcgaagcc tccaggcctt tttggccata    120
gctgcccggg tctttgccca cggagcagca actctgactg agcccttagt gccaacagct    180
taaggatgcc caggttccca tggctaccat gataagacta atctatcagc ccagacatct    240
accagttaat taacccatta ggacttgtgc tgttcttgtt tcgtttgttt tgcgtgaagg    300
gcaaggacac cattattaaa gagaaaagaa acaaacccca gagcaggcag ctggctagag    360
aaaggagctg gagaagaaga ataaagtctc gagcccttgg ccttggaagc gggcaagcag    420
ctgcgtggcc tgaggggaag ggggcggtgg catcgagaaa ctgtgagaaa acccagagca    480
tcagaaaaag tgagcccagg ctttggccat tatctgtaag aaaacaaga aaggggaac      540 attatacttt cctgggtggc tcagggaaat gtgcagatgc acagtactcc agacagcagc    600
tctgtacctg cctgctctgt ccctcagttc taacagaatc tagtcactaa gaactaacag    660
gactaccaat acgaactgac aaatactacc actatgacct gtgacaaagc tgtttattta    720
ttaagtggga agggaacttt tgatattatt tatccttgta acagtataga tgatggttat    780
ttattctatt tataaggaat tatgtatttt ttttttcaata aagatttatt tatgtggctc    840
tctgggtcta aatttctaag tgtagtcggg agagaaaaga gatg                    884

<210> SEQ ID NO 8
<211> LENGTH: 21
<212> TYPE: DNA
<213> ORGANISM: Mus musculus

<400> SEQUENCE: 8
```

-continued ctaagccgat gttgatgtgt c                                    21

<210> SEQ ID NO 9
<211> LENGTH: 25
<212> TYPE: DNA
<213> ORGANISM: Mus musculus

<400> SEQUENCE: 9
gcagatgcac agtactccag acagc                                25

<210> SEQ ID NO 10
<211> LENGTH: 38
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 10
gtcgactgca gtctagacta agccgatgtt gatgtgtc                  38

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 11
gctgtctgga gtactgtgca tctgc                                25

<210> SEQ ID NO 12
<211> LENGTH: 34
<212> TYPE: DNA
<213> ORGANISM: Artificial Sequence
<220> FEATURE:
<223> OTHER INFORMATION: Description of Artificial Sequence:Artificially
      Synthesized Sequence

<400> SEQUENCE: 12
ataacttcgt atagcataca ttatacgaag ttat                      34

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 13
gctgtctgga gtactgtgca tctgc                                25

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 14
ccgtgatatt gctgaagagc ttggc                                25

<210> SEQ ID NO 15

```
<211> LENGTH: 21
<212> TYPE: PRT
<213> ORGANISM: Artificial Sequence
<220> FEATURE:
<223> OTHER INFORMATION: Description of Artificial Sequence:Artificially
      Synthesized Peptide

<400> SEQUENCE: 15

Met Glu Val Gly Trp Tyr Arg Ser Pro Phe Ser Arg Val Val His Leu
 1               5                  10                  15

Tyr Arg Asn Gly Lys
            20
```

SGRF GENE-MODIFIED MOUSE

CROSS-REFERENCE TO RELATED APPLICATIONS

This application is a continuation of U.S. Ser. No. 10/493,526, filed on Oct. 6, 2004 now abandoned, which is the National Stage of International Application No. PCT/JP02/11047, filed on Oct. 24, 2002, which claims priority to Japanese Patent No. 2001-326858, filed on Oct. 24, 2001, all of which are incorporated herein by reference in their entireties.

TECHNICAL FIELD

The present invention relates to SGRF gene knockout non-human animals and cells, and to uses thereof.

BACKGROUND ART

SGRF (Interleukin-Six, G-CSF Related Factor)/IL-23 (hereafter indicated as "SGRF") is a novel cytokine cloned by the present inventors based on an EST (Patent number EP1072610, GenBank Accession No. AB030000). Oppmann et al. also isolated this gene using similar methods, reporting it as a novel cytokine (p19/IL-23) that exerts its physiological function by combining with the p40 subunit of IL-12 (Immunity Vol. 13, p 715, 2000). However, to date the physiological function of this gene has been unclear, except for the following: (1) it induces proliferation of $CD4^+CD45RB^{low}$ T cells in mice, and (2) it induces IFN-γ production in human memory T cells. Analysis using IL-12 p40 deficient mice (knockout mice) and research using an antibody against IL-12 p40 has introduced the possibility that functions conventionally attributed to IL-12 could in fact be due to SGRF function.

The present inventors sought effective experimental systems for use in elucidating the functions of the SGRF gene, which were as yet unknown. Genetically modified animals in which SGRF gene allele inactivation lead to lack of SGRF enzymatic activity, or cell lines derived from these genetically modified animals, or ES cell lines can be utilized to elucidate the physiological function of SGRF at both the cellular and whole individual levels. Thus, such animals and cell lines can be used to develop therapeutic drugs to treat diseases associated with the SGRF gene.

DISCLOSURE OF THE INVENTION

The present invention was carried out under such circumstances. An object of the present invention is to provide genetically modified animals in which both SGRF gene alleles have been inactivated, and therefore to provide animals which do not possess SGRF activity. Another object of the present invention is to provide cell lines derived from these animals, ES cells in which expression of the SGRF gene has been suppressed, as well as screening methods for compounds that substitute for SGRF function in these animals. Another object of the present invention is to provide therapeutic drugs for diseases associated with SGRF, based on observations of SGRF function obtained using these genetically modified mice.

The present inventors generated SGRF gene-modified animals in order to achieve the above-described objectives. SGRF gene exon region was replaced with appropriate drug marker genes, thereby generating a targeting vector. This targeting vector was transfected into mouse-derived ES cell lines, and then cell lines in which homologous recombination had occurred were selected. ES cells in which one of the SGRF gene alleles was inactivated were injected into a C57BL/6J mouse-derived blastocyst, and chimeric mice were obtained. Mice in which one of the SGRF gene alleles had been inactivated (SGRF/IL-23$^{+/-}$) were obtained by crossing these chimeric mice with C57BL/6J mice. Mice in which both SGRF gene alleles were inactivated (SGRF/IL-23$^{-/-}$) were successfully obtained by crossing SGRF/IL-23$^{+/-}$ mice with each other.

Such genetically modified animals and ES cells can be used to predict the side effects of SGRF inhibitors, including, for example, anti-SGRF antibodies or SGRF antagonists. In addition, the genetically modified animals and ES cells of this invention can be used to examine whether or not test proteins and small molecules have the ability to substitute for SGRF function, and also to screen for DNAs that encode proteins comprising the ability to substitute for SGRF function.

The present inventors used the above-described genetically modified animals to reveal the association of SGRF's physiological functions with disease. For example, the genetically modified mice were found to be susceptible to infection by the pathogenic microbe, *Listeria*. Therefore, SGRF may be a therapeutic drug for pathogenic microbes. The induction of experimental autoimmune encephalomyelitis (EAE) does not easily occur in genetically modified mice, and had a low delayed-type hypersensitivity response. Therefore, it is suggested that SGRF is associated with the development of autoimmune and inflammatory diseases in humans. Hence, compounds that inhibit SGRF function are expected to be drugs for treating autoimmune or inflammatory diseases.

SGRF is expressed in the brain, and SGRF/IL-23$^{-/-}$ mice do not easily develop EAE, indicating involvement of SGRF in encephalopathy. Therefore, compounds that inhibit SGRF function are expected to be drugs for treating encephalopathy.

Thus, the present invention relates to genetically modified animals in which SGRF gene allele inactivation has eliminated SGRF enzymatic activity, cell lines derived from these animals, and ES cells in which expression of the SGRF gene is suppressed. The present invention also relates to uses for screening compounds that can substitute for SGRF function using these animals, and to therapeutic drugs for diseases associated with SGRF. More specifically, the present invention provides:

(1) a genetically modified non-human animal in which SGRF gene expression is artificially suppressed;

(2) a genetically modified non-human animal in which a foreign gene is inserted into one or both of the SGRF gene alleles;

(3) the genetically modified animal of (1) or (2), in which the non-human animal is a rodent;

(4) the genetically modified animal of (3), in which the rodent is a mouse;

(5) a cell line established from a genetically modified animal of any one of (1) to (4);

(6) a method for producing an anti-SGRF antibody, wherein the method comprises using a genetically modified animal of any one of (1) to (4);

(7) a non-human ES cell in which SGRF gene expression is artificially suppressed;

(8) a non-human ES cell in which a foreign gene is inserted into one or both of the SGRF gene alleles;

(9) the ES cell of (7) or (8), in which the non-human ES cell is a rodent ES cell;

(10) the ES cell of (9), in which the rodent ES cell is a mouse ES cell;

(11) an infection-preventing agent, comprising a compound that can substitute for SGRF or a SGRF signal, as its active ingredient;

(12) a therapeutic agent for autoimmune diseases, which comprises an SGRF antagonist as its active ingredient;
(13) a therapeutic agent for inflammatory diseases, which comprises an SGRF antagonist as its active ingredient;
(14) the therapeutic agent of (12) or (13), in which the antagonist is an anti-SGRF antibody;
(15) a method of screening for a compound as a candidate for a therapeutic agent for autoimmune or inflammatory diseases, wherein the method comprises the steps of (a) to (c):

(a) contacting SGRF with a test compound;

(b) measuring the binding activity of SGRF with a test compound;

(c) selecting a compound which binds to SGRF;
(16) a method of screening for a compound which can substitute for SGRF protein function, wherein the method comprises the steps of (a) to (c):

(a) administering a test compound into a genetically modified animal of any one of (1) to (4);

(b) determining whether the test compound can substitute for SGRF function;

(c) selecting a compound that can substitute for SGRF function.

The present invention provides genetically modified non-human animals and ES cells characterized by artificial suppression of SGRF gene expression.

The SGRF (Interleukin-Six, G-CSF Related Factor) gene (the protein encoded by this gene is described as "SGRF") of the present invention has been identified in, for example, humans (GenBank Accession No. ABO30000) and mice (GenBank Accession No. AF301619). The SGRF gene consists of four exons (GenBank Accession No. ABO30001). In the present invention, "SGRF gene expression is artificially suppressed" means that the expression of the SGRF gene is suppressed due to genetic mutation, including insertion, deletion, or substitution of nucleotides into one or both of the SGRF gene alleles. Cases where the function of the normal SGRF protein is reduced or lost due to the expression of a mutant SGRF protein are also included in "suppression of SGRF gene expression". "Suppression" as described above includes both cases where SGRF gene expression is completely suppressed, and where expression of only one SGRF gene allele is suppressed. In the present invention, specific suppression of SGRF gene expression is preferred. There is no restriction as to the sites into which mutations can be introduced, as long as gene expression is suppressed. For example, mutations can be introduced into exons or promoter regions.

Animals used for SGRF gene modification in the present invention are usually animals other than humans, preferably rodents such as mice, rats, hamsters and rabbits, and more preferably mice. ES cells used for SGRF gene modification in the present invention are preferably derived from rodents, and more preferably from mice. Furthermore, animals generally referred to as "knockout animals" are also included as genetically modified animals of the present invention.

In the present invention, methods for artificially suppressing the SGRF gene in genetically modified ES cells and genetically modified non-human animals (also referred to as "genetically modified animals") include deletion of part of or the entire SGRF gene, or deletion of part of or the entire SGRF gene expression regulatory region. Inactivation of the SGRF gene by the insertion of a foreign gene into one or both of the SGRF gene alleles is preferable. Therefore, in a preferred embodiment of the present invention, a genetically modified animal or genetically modified ES cell is characterized by the insertion of a foreign gene into one or both of the SGRF gene alleles.

The genetically modified animal of the present invention can be constructed using genetic engineering techniques well known to those skilled in the art. For example, a genetically modified mouse can be constructed as follows: First, DNA including the exons of the SGRF gene is isolated from a mouse. A targeting vector is then constructed by inserting an appropriate marker gene into this DNA fragment. This targeting vector is introduced into a mouse ES cell line using electroporation or the like, and a cell line in which homologous recombination has occurred is selected. The marker gene to be inserted is preferably a gene that is resistant to an antibiotic, such as the neomycin-resistant gene. When such an antibiotic-resistant gene is inserted, a cell line in which homologous recombination has occurred can be easily selected by simply incubating the cells in a medium containing the antibiotic. For a more effective selection, a gene such as the thymidine kinase gene can also be inserted into the targeting vector. This procedure allows exclusion of cell lines in which non-homologous recombination has occurred. Moreover, a cell line in which one of the SGRF gene alleles has been inactivated can be efficiently obtained by selecting homologous recombinants using PCR and Southern blotting.

When cell lines produced by homologous recombination are selected, chimeras are preferably constructed using multiple clones, because gene insertion at sites other than homologous recombination sites may have destroyed unknown genes. Chimeric mice can be produced by injecting the obtained ES cell line into mice blastocysts. Mice in which one SGRF allele is inactivated can be obtained by crossing these chimeric mice with wild type mice. By crossing the offspring of these crosses with each other, mice can be obtained in which both SGRF alleles have been inactivated. More specifically, it is possible to construct a genetically modified mouse of the present invention according to the method described below in the Examples. In addition to mice, it is also possible to genetically modify other animals in which ES cells have been established.

An ES cell line in which both SGRF alleles are inactivated can be created by incubating an ES cell line in which one locus is inactivated in a selective medium comprising a high concentration of an antibiotic, upon which the other locus is inactivated. The above-mentioned ES cell line can also be constructed by selecting an ES cell line in which one locus is inactivated, reintroducing the targeting vector into this cell line, and selecting a cell line in which homologous recombination has occurred. The marker gene to be inserted into the targeting vector is preferably different to that used previously.

The present invention also provides cell lines established from the genetically modified non-human animals of the present invention. Cell lines can be established from the genetically modified animals of the present invention using conventional methods. For example, a primary culture method for embryonic cells can be used in the case of rodents (Shin-seikagaku Jikken Kouza, vol. 18, pp 125-129, Tokyo Kagaku Doujin; and "Manuals for manipulating mouse embryos", pp 262-264, Kindai Shuppan).

The genetically modified animals, cell lines established from these animals, and ES cell lines of the present invention can be used for detailed functional analysis of SGRF genes. For example, the genetically modified animals, cell lines established from these animals, and ES cell lines of the present invention can be used for predicting the side effects of SGRF inhibitors such as anti-SGRF antibodies or SGRF antagonist small molecules. SGRF inhibitors (antagonists)

are not considered to have lethal side effects since the genetically modified mice obtained from the present invention grew normally and did not die, at least during fetal development. SGRF inhibitor side effects may also be predicted by detailed examination of the genetically modified animals of the present invention. SGRF inhibitor side effects in each tissue can be precisely examined by using cell lines established from tissues of the genetically modified animals. Moreover, genetically modified animals of the present invention can be used to screen for compounds that can substitute for the function of the SGRF protein, as described below.

In the genetically modified animals of the present invention, the SGRF gene is inactivated from birth, and thus the animal can efficiently produce antibodies against SGRF-binding proteins such as SGRF or IL-12 p40. For example, it is possible to efficiently produce monoclonal or polyclonal antibodies against SGRF by immunizing a genetically modified mouse of the present invention with SGRF together with Freund's complete adjuvant. In this case, the SGRF used for immunization can be derived from a rat or a human, as well as a mouse.

Observation of the symptoms of the genetically modified animals of this invention, and comparison of these symptoms with the symptoms of diseases of unknown cause, will reveal if a disease is caused by SGRF malfunction. For example, phenotypes characteristically appearing in genetically modified mice or cell lines derived from these mice, can be compared with various symptoms of human disease. If more than half of the symptoms of a human disease are observed in the genetically modified mice of this invention, it can be presumed that the disease may be due to SGRF malfunction.

As described in the Examples below, the present inventors revealed SGRF's physiological function and association with disease by generating and analyzing mice with an inactivated SGRF gene (SGRF KO mice). These SGRF KO mice are susceptible to infection with the pathogenic microbe *Listeria*. Therefore, SGRF and alternative substances involved in SGRF signaling are expected to be drugs against pathogenic microbes. Thus, the present invention provides infection-preventing drugs that comprise SGRF as an active ingredient.

Induction of experimental autoimmune encephalomyelitis (EAE) is difficult in SGRF KO mice. SGRF is suspected to be an important factor in the development of human autoimmune diseases, including multiple sclerosis (MS), and can be a target for treating such autoimmune diseases. Thus, SGRF antagonists are expected to be drugs for treating autoimmune diseases. Therefore, the present invention provides therapeutic drugs for autoimmune diseases which comprise an SGRF antagonist as an active ingredient.

SGRF KO mice have reduced delayed-type hypersensitivity, as described in the Examples. Thus, suppression of SGRF function can be a target for treating various inflammatory diseases, such as asthma and allergies. Therefore, the present invention also provides therapeutic drugs for inflammatory diseases which comprise an SGRF antagonist as an active ingredient.

The present invention also provides therapeutic drugs for encephalopathy which comprise an SGRF antagonist as an active ingredient.

SGRF antagonists of the present invention include, for example, anti-SGRF antibodies and anti-IL-12 p40 antibodies. SGRF antagonists can be screened, for example, via the following method:

Ba/F3 cells are known to react with IL-23, causing proliferation when IL-12β1 and IL-23R are transfected into Ba/F3 cells (J. Immunol., Vol. 168, p. 5699-5708, (2002)). Therefore, a test compound that specifically inhibits IL-23 dependent proliferation of such cell strains can be isolated as an antagonist.

STAT4 phosphorylation is known to occur on addition of SGRF to PHA-activated human premature T cells. In this system, compounds which suppress STAT4 phosphorylation in the presence of SGRF, are considered antagonist candidates. Therefore, SGRF antagonists can be screened by contacting SGRF and a test compound with PHF-activated premature T cells, and then selecting compounds which suppress STAT4 phosphorylation.

Autoimmune diseases as mentioned above include, multiple sclerosis, chronic rheumatoid arthritis, autoimmune colitis, psoriasis, Crohn's disease, ulcerative colitis, encephalomyelitis, polymyositis, dermatomyositis, chronic inflammatory demyelinating polyradiculitis, insulin-dependent diabetes, spontaneous thrombocytopenic peliosis, systemic lupus erythematosus, autoimmune hemolytic anemia, myasthenia gravis, Kawasaki disease, and habitual abortion. Inflammatory diseases include, for example, asthma, allergies, hepatitis, arthritis (spinal arthritis and chronic rheumatoid arthritis), gouty arthritis, asteoarthritis, bronchitis, menstrual cramps, tendonitis, bursitis, dermatitis, rash, psoriasis, burn, inflammatory bowel disease, Crohn's disease, gastritis, irritable colon syndrome, ulcerative colitis, polyarteritis nodosa, thyroiditis, aplastic anemia, Hodgkin's disease, scleroderma, rheumatoid fever, sarcoidosis, nephrosis syndrome, Behcet's syndrome, polymyositis, gingivitis, hypersensitivity, conjunctivitis, and myocardial ischemia.

"SGRF" in the therapeutic agents of the present invention can be prepared as a natural protein, or as a recombinant protein obtained by well-known genetic recombination techniques. There is no restriction as to the organism from which the "SGRF" of the therapeutic agents of the present invention can be derived. When SGRF is used for the treatment and prevention of human disease, it is preferably derived from mammals, and most preferably from humans. SGRF can be prepared as a natural protein by using anti-SGRF antibody-coupled affinity chromatography, using extracts from tissues expected to express SGRF, such as, testis, lymph nodes, and the thymus.

A recombinant protein can be prepared, for example, as a recombinant polypeptide by methods well known to those skilled in the art. The recombinant polypeptide can be prepared by inserting a DNA (for example, a DNA encoding the SGRF gene) into an appropriate expression vector, transfecting this vector into appropriate host cells, collecting transformants thus obtained, and then purifying the polypeptide after obtaining an extract using chromatography such as ion exchange chromatography, reverse phase chromatography, gel filtration chromatography, or affinity chromatography, wherein antibodies against the mutant of this invention are fixed onto a column. A number of these columns may be used in combination.

When SGRF is expressed in a host cell (for example, an animal cell, *E. coli*, etc.) as a polypeptide fused with glutathione S-transferase protein, or as a recombinant polypeptide combined with a number of histidines, the expressed recombinant polypeptide can be purified using a glutathione column or a nickel column.

When *E. coli* is the host cell, there is no limitation as to the above-described vector, as long as it comprises an "ori" and a marker gene, where the "ori" is for amplifying and mass-producing the vector in *E. coli* (e.g., JM109, DH5α, HB101, or XL1Blue), and the marker gene is for selecting the transformed *E. coli* (e.g., a drug-resistance gene can be selected using a drug (e.g., ampicillin, tetracycline, kanamycin, or chloramphenicol)). For example, M13-series vectors, pUC-series vectors, pBR322, pBluescript, pCR-Script, and such can be used. In addition to these vectors, pGEM-T, pDIRECT, pT7, and the like can also be used for subcloning and excising the cDNA. When using a vector to produce SGRF, an expression vector is especially useful. When the expression vector is expressed in *E. coli*, it should comprise the above characteristics in order to be amplified in *E. coli*. Additionally, when *E. coli* such as JM109, DH5α, HB101 or XL1-Blue are used as the host cell, the vector should comprise a promoter which can efficiently promote expression of the desired gene in *E. coli*, e.g., the lacZ promoter (Ward et al. (1989) Nature 341: 544-546; (1992) FASEB J. 6:2422-2427), araB promoter (Better et al. (1988) Science 240:1041-1043), or T7 promoter. Other examples of the vectors include pGEX-5X-1 (Pharmacia), "QIAexpress system" (QIAGEN), pEGFP, and pET.

The vector may comprise a signal sequence for secreting the polypeptide. The signal sequence for secretion of the polypeptide into the periplasm of *E. coli* can be the pelB signal sequence (Lei, S. P. et al. (1987) J. Bacteriol. 169: 4379). For example, electroporation or the calcium chloride method may be used to introduce the vector into host cells.

Other vectors for use in producing SGRF, other than those derived from *E. coli*, include expression vectors derived from mammals (e.g., pCDNA3 (Invitrogen), PEGF-BOS (Nucleic Acids Res. (1990) 18(17):5322), pEF, pCDM8), insect cells (e.g., "Bac-to-Bac baculovirus expression system" (GIBCO-BRL), pBacPAK8), plants (e.g., pMH1, pMH2), animal viruses (e.g., PHSV, pMV, pAdexLcw), retroviruses (e.g., pZIPneo), yeasts (e.g., "Pichia Expression Kit" (Invitrogen), pNV11, SP-Q01), and *Bacillus subtilis* (e.g., pPL608, pKTH50).

In order to express proteins in animal cells such as CHO, COS, and NIH3T3 cells, the vector must comprise a promoter necessary for expression in such cells (e.g., the SV40 promoter (Mulligan et al. (1979) Nature 277:108), MMLV-LTR promoter, EFla promoter (Mizushima et al. (1990) Nucleic Acids Res. 18:5322), CMV promoter, etc.). The vector preferably comprises an additional marker gene for selecting transformants (for example, a drug resistance gene can be selected using a drug (e.g., neomycin, G418, etc.)). Examples of vectors with such characteristics include pMAM, pDR2, pBK-RSV, pBK-CMV, pOPRSV, pOP13, etc.

Systems for in vivo polypeptide production include those using animals and plants. A DNA encoding SGRF can be introduced into this animal or plant, where the SGRF is produced in vivo and then recovered.

Animals for use in the production system described above include mammals and insects. Mammals such as goats, pigs, sheep, mice and cattle may be used (Vicki Glaser (1993) SPECTRUM Biotechnology Applications). Alternatively, the mammals may be transgenic animals.

For instance, a DNA encoding SGRF may be prepared as a fusion gene with a gene such as goat β casein gene that encodes a polypeptide specifically produced in milk. DNA fragments comprising the fusion gene are injected into goat embryos, which are then introduced back into female goats. SGRF can be obtained from milk produced by the transgenic goats born from those that received the modified embryos, or from their offspring. Appropriate hormones may be administered to increase the amount of polypeptide-containing milk produced by the transgenic goats (Ebert, K. M. et al., (1994) Bio/Technology 12:699-702).

Alternatively, insects such as the silkworm may be used. Baculoviruses, into which a DNA encoding SGRF has been inserted, can be used to infect silkworms, and SGRF can then be recovered from the body fluid and silk (Susumu M. et al., (1985) Nature 315:592-594).

When using plants, tobacco can be used as an example. In the case of tobacco, a DNA encoding SGRF may be inserted into a plant expression vector such as pMON 530, which is introduced into bacteria such as *Agrobacterium tumefaciens*. These bacteria are then used to infect tobacco plants such as *Nicotiana tabacum*, and desired mutants are recovered from the leaves (Julian K.-C. Ma et al., Eur. J. Immunol. 24:131-138 (1994)).

SGRF obtained as above may be isolated inside or outside (e.g., from the medium) of host cells, and purified as a substantially pure homogeneous polypeptide. The method for polypeptide isolation and purification is not limited to any specific method. In fact, any standard method may be used. For instance, column chromatography, filters, ultrafiltration, salting out, solvent precipitation, solvent extraction, distillation, immunoprecipitation, SDS-polyacrylamide gel electrophoresis, isoelectric point electrophoresis, dialysis, and recrystallization may be appropriately selected and combined to isolate and purify the polypeptide.

SGRF of the present invention may be optionally modified or partially deleted by treatment with an appropriate protein-modifying enzyme, before or after purification. For example, trypsin, chymotrypsin, lysylendopeptidase, protein kinase, glucosidase, and the like can be used as protein-modifying enzymes.

The above-mentioned anti-SGRF antibody of the present invention is not restricted, and monoclonal or polyclonal antibodies may be used. In addition, antiserum obtained by immunizing an animal such as a rabbit with SGRF, all classes of polyclonal and monoclonal antibodies, human antibodies, and humanized antibodies produced by genetic recombination, are all included in the above anti-SGRF antibody. The above-mentioned antibodies can be prepared by the following methods. For example, a polyclonal antibody can be prepared as follows: Small animals such as rabbits are immunized with SGRF to obtain serum, a serum fraction which recognizes only SGRF is collected using SGRF-coupled affinity column chromatography, and immunoglobulin G or M are then purified from this fraction using protein A or protein G columns to obtain polyclonal antibodies. A monoclonal antibody can be prepared as follows: Small animals such as mice are immunized with SGRF, the spleen is excised from the animal and gently crushed to separate cells, these cells are fused with mouse myeloma cells using reagents such as polyethylene glycol, and clones that produce antibodies against SGRF are selected from these fused cells (hybridomas). Next, the obtained hybridomas are transplanted into the peritoneal cavity of a nude mouse, and ascites are collected from the mouse. Monoclonal antibodies can be prepared by purifying these ascites using, for example, ammonium sulfate precipitation, protein A or protein G column chromatography, DEAE ion exchange chromatography, or SGRF-coupled affinity column chromatography. The above-mentioned antibodies can be used for purification and identification of SGRF, and can be used as drugs to control SGRF function. Human antibodies or humanized antibodies are effective when using antibodies as therapeutic drugs for humans, taking antigenicity into account. Human antibodies or humanized antibodies can be prepared by methods well known to those skilled in the art. For example, human antibodies can be prepared by using SGRF to immunize mice whose immune system has been replaced with a human immune system. Alternatively, human antibodies can be prepared by panning from a phage library comprising human antibodies. Humanized antibodies can be obtained, for example, using CDR graft methods in which the antibody gene is cloned from monoclonal antibody-producing cells, and its antigenic determinant site is grafted into an existing human antibody.

The present invention also provides a method of screening for candidate therapeutic drug compounds to treat autoimmune or inflammatory disease. The screening method of the present invention includes the following steps: (a) contacting SGRF with a test compound; (b) measuring SGRF binding activity with a test compound; and (c) selecting compounds that bind to SGRF.

The screening method of the present invention can also be used for screening therapeutic drugs for encephalopathy.

Test compounds that can be used for screening are not restricted. For example, synthetic small molecule compound libraries, purified proteins, gene library expression products, synthetic peptide libraries, cell extracts, and cell culture supernatants can be used. SGRF binding activity with a test compound can be measured using methods well known to those skilled in the art.

Screening for proteins that bind to SGRF may be carried out using, for example, West-Western blotting (Skolnik E Y, Margolis B, Mohammadi M, Lowenstein E, Fischer R, Drepps A, Ullrich A, and Schlessinger J (1991) Cloning of P13 Kinase-associated p85 utilizing a novel method for expression/cloning of target proteins for receptor tyrosine kinases. Cell 65, 83-90). Specifically, phage vectors (λgt11, ZAP11, etc) are used to construct a cDNA library from cells or tissues (for example, the testis, lymph node, or thymus) in which a protein binding to a protein of the present invention is expected to be expressed. This library is then expressed on LB-agarose and transferred to a filter membrane, which is then reacted with purified biotin-labeled or GST-fused protein of the present invention. The plaques expressing proteins that bind to a protein of the present invention can be detected by using streptavidin, anti-GST antibody, or the like.

Alternatively, screening for SGRF-binding proteins or genes encoding these proteins can be performed according to "a two-hybrid system" ("MATCHMAKER Two-Hybrid System", "Mammalian MATCHMAKER Two-Hybrid Assay Kit", "MATCHMAKER One-Hybrid System" (all products by Clontech), "HybriZAP Two-Hybrid Vector System" (Stratagene), literature [Dalton S., and Treisman R., Characterization of SAP-1, a protein recruited by serum response factor to the c-fos serum response element. Cell 68, 597-612 (1992)]). The two-hybrid system can be performed as follows: SGRF is fused to an SRF- or Gal4-binding domain, and expressed in yeast cells; a cDNA library, which expresses proteins as fusion proteins with the VP16 or Gal4 transcription activation domain, is prepared from cells expected to express proteins binding to SGRF; the library is introduced to the above-mentioned yeast cells; and library-derived cDNA are isolated from the positive clones detected (positive clones can be confirmed by reporter gene activation due to the binding of SGRF and the protein when expressed in the yeast cells). The protein encoded by the isolated cDNA can be obtained by introducing and expressing that cDNA in *E. coli*.

Screening for SGRF-binding proteins can also be performed by applying cell extracts or culture supernatants expected to express SGRF-binding proteins, onto a SGRF-coupled affinity chromatography column, and purifying proteins that specifically bind to this column.

Small molecule compounds, proteins (or genes encoding these proteins), peptides, and such, which bind to SGRF can be isolated using methods well known to those skilled in the art. Such methods include, for example, screening for binding-molecules by contact with synthetic compounds, natural product banks, or random phage peptide display libraries with an immobilized SGRF; and high-throughput screening methods using combinatorial chemistry techniques (Wrighton N C; Farrell F X; Chang R; Kashyap A K; Barbone F P; Mulcahy L S; Johnson D L; Barrett R W; Jolliffe L K; Dower W J., Small peptides as potent mimetics of the protein hormone erythropoietin, Science (United States) July 26, 273 p 458-64 (1996), Verdine G L., The combinatorial chemistry of nature. Nature (England) November 7, 384 p 11-13 (1996), Hogan J C Jr., Directed combinatorial chemistry. Nature (England) November 7, 384 p 17-9 (1996)).

The present invention also provides methods of screening for compounds that can substitute for SGRF protein function, where the methods use genetically modified animals of the present invention. The above-mentioned screening methods include the following steps: (a) administrating a test compound to a genetically modified animal of the present invention; (b) determining whether the test compound substitutes for SGRF function; and (c) selecting compounds that can substitute for SGRF function.

Administration of the test compound to a genetically modified animal of (a) can be performed orally or parenterally. Examples of conditions that can be used to determine whether a test compound substitutes for SGRF function include the following:

(1) on administration of the test compound, a genetically modified animal of the present invention originally susceptible to pathogenic microbes such as *Listeria*, gains resistance to such microbes;

(2) on administration of the test compound, symptoms of autoimmune diseases such as EAE are induced in a genetically modified animal of the present invention, although induction of such autoimmune diseases in the animal was originally difficult;

(3) on administration of the test compound, a genetically modified animal of the present invention originally displaying mild symptoms of inflammatory disease, such as delayed-hyper sensitivity, develops an inflammatory disease or the symptoms are worsened;

(4) jak or STAT is phosphorylated when a test compound is added to cultured cells derived from primary or passaged cultures of SGRF receptor-expressing cells (for example, human T cell blastocysts), taken from a genetically modified animal of the present invention (or a normal animal);

(5) IL-23 dependent proliferation of IL-12Rβ1- and IL-23R-transfected Ba/F3 cells is specifically inhibited. (When IL-12Rβ1 and IL-23R are transfected into Ba/F3 cells, these cells proliferate by reacting to IL-23.)

Whether resistance to pathogen infection has been conferred in the above-mentioned (1) can be assessed, for example, by comparing pathogen infection of mice in which both SGRF gene alleles are inactivated, with that of normal individuals in which SGRF is not inactivated (SGRF/IL-23$^{+/+}$). *Listeria* and such are often used for this type of mouse infection study. However, infections by pathogenic microbes other than *Listeria*, such as pathogenic *E. coli, Salmonella*, and *Staphylococcus*, or viruses such as Vascular Stomatitis Virus (VSV), Lymphocytic Choriomeningitis Virus (LCMV), and influenza, or parasites such as *Leishmania* and Japanese Schistosomiasis, can be used for comparison. The above-described pathogenic microbes used for assessment of SGRF involvement in defense mechanisms are not limited to those that infect mice. Microbes that can infect other animals, such as HTLV-I, HCV, HBV or HIV, can also be used for assessment.

A case such as that above in (2) can be assessed by using well-known immunological methods to induce a disease model in a genetically modified mice of the present invention, and then comparing these with normal individuals. For example, experimental autoimmune encephalomyelitis (EAE) is known to be a model for human multiple sclerosis. Collagen-induced arthritis is known as a model for human chronic rheumatoid arthritis, and Dextran sodium sulfate-induced colitis is known as a model for colitis. Assessment can also be performed using a human systemic erythematodis model or a diabetes model, by breeding with known lpr/lpr mice, which develop autoimmune disease naturally, or with NOD mice or the like.

In the above-mentioned (3), assessment can be performed by using well-known immunological methods to induce a disease model in a genetically modified mice of the present invention, and then comparing it with a normal mouse. For example, an asthma model can be established by re-sensitizing OVA through the respiratory tract after immunization. Alternatively, hepatitis can be induced by injecting concanavallin A into mouse-tail veins. Delayed Type Hypersensitivity (DTH) is a general inflammation model.

SGRF, antagonists against SGRF, anti-SGRF antibodies, or compounds that can be isolated using the screening methods of the present invention, can be used as pharmaceutical agents for humans and non-human animals by directly administering the isolated compound to the patient, or by formulating and administering it according to pharmacologically accepted methods. For example, the compound(s) may be orally administered as tablets (sugarcoated as necessary), capsules, elixirs, or microcapsules. It may also be parenterally administered as injections of an aseptic solution or suspension with water or another pharmaceutically acceptable liquid. For example, by suitably mixing a pharmaceutical composition with a pharmacologically acceptable carrier or medium, a unit dosage form such as one generally required for drug implementation can be formulated. Specific examples of a pharmacologically acceptable carrier or medium include sterilized water, physiological saline, vegetable oil, an emulsifier, suspension agent, surfactant, stabilizer, flavoring agent, excipient, vehicle, antiseptic, binder, and so on. The amount of active ingredient in these preparations is adjusted to obtain a suitable volume within a specified range.

Examples of additives that can be mixed into tablets and capsules include binders such as gelatin, cornstarch, gum tragacanth, and gum arabic; excipients such as crystalline cellulose; swelling agents such as cornstarch, gelatin, and alginic acid; lubricants such as magnesium stearate; sweeteners such as sucrose, lactose, and saccharin; and flavoring agents such as peppermint, *Gaultheria adenothrix* oil, and cherry flavoring. When the preparation unit is in the form of a capsule, liquid carriers such as fats and oils can be included in addition to the above materials. Aseptic compositions for injections can be formulated according to ordinary preparation methods, using vehicles such as distilled water for injection.

Examples of aqueous solutions suitable for injections include physiological saline, and isotonic liquids containing glucose or other adjuvants, such as D-sorbitol, D-mannose, D-mannitol, and sodium chloride. These may be used in combination with suitable solubilizers, for example, alcohols such as ethanol; polyalcohols including propylene glycol and polyethylene glycol; and nonionic surfactants such as Polysorbate 80 (™) and HCO-50.

Examples of oleaginous liquids include sesame oil and soybean oil, and these may be used in combination with solubilizers such as benzyl benzoate and benzyl alcohol. In addition, the blend may include buffers such as phosphate buffer and sodium acetate buffer; analgesics such as procaine hydrochloride; stabilizers such as benzyl alcohol and phenol; and antioxidants. The prepared injection liquid is normally filled into suitable ampules.

Administration to patients can be carried out using standard methods known to those skilled in the art, such as, by intra-arterial injection, intravenous injection or subcutaneous injection; or by intranasal, transbronchial, intramuscular, percutaneous or oral administration. Dosage varies depending on a patient's body weight and age, administration method, and so on; however, an appropriate dosage can be suitably selected by a person skilled in the art. If the compound can be encoded by a DNA, gene therapy may also be carried out by incorporating the DNA into a vector for gene therapy. Dosage and administration method vary according to a patient's body weight, age, and symptoms, but can be suitably selected by a person skilled in the art.

Although compound dosage varies according to symptoms, orally administered dosage for an adult (with a body weight of 60 kg) typically ranges from about 0.1 to 100 mg per day, preferably about 1.0 to 50 mg per day, and more preferably about 1.0 to 20 mg per day.

Although parenterally administered dosage varies according to the target organ, symptoms, administration method, and subject to be administered, a single dosage in the form of an injection preparation for an adult of body weight 60 kg, for example, is normally about 0.01 to 30 mg per day, preferably about 0.1 to 20 mg per day, and more preferably about 0.1 to 10 mg per day. Administration is preferably carried out by intravenous injection. When administering to other animals, doses adjusted per 60 kg body weight or per body surface area can be administered.

BRIEF DESCRIPTION OF THE DRAWINGS

Wild type mice in the figures are represented as Wt. SGRF/IL-23$^{-/-}$ mice are represented as KO.

FIG. 1 shows the genomic nucleotide sequence of the mouse SGRF.

FIG. 2 shows the continuation of the genomic nucleotide sequence of the mouse SGRF.

a. A photograph depicting the results of Northern blot analysis of mouse SGRF transcripts. PolyA$^+$ RNA (5 µg) used for Northern blot hybridization was prepared from tissues (brain, heart, thymus, lung, liver, spleen, lymph nodes, kidney, and testis) of C57BL/6 mouse (male, four weeks old). β-Actin was used as a reference.

b. A drawing depicting the structures of the mouse SGRF gene and gene-targeting vector. A targeting vector was generated by replacing two SGRF gene exons with a neomycin resistant gene (neo), located between loxP sites. The diphtheria toxin A (DT-A) fragment gene is placed outside of the 3' genomic DNA fragment. In the figure, exons are filled boxes, and loxP sites are filled triangles.

c. A photograph depicting the result of southern blot analysis of EcoR I-digested genomic DNA. After homologous recombination, the mutated allele was detected using an EcoRI cleavage site introduced into the neo gene.

d. A photograph showing the results of RT-PCR analysis of polyA$^+$ RNA isolated from thymus. The photograph shows PCR products of SGRF from mice of each SGRF genotype and those of GAPDH as a control.

Figure 4:
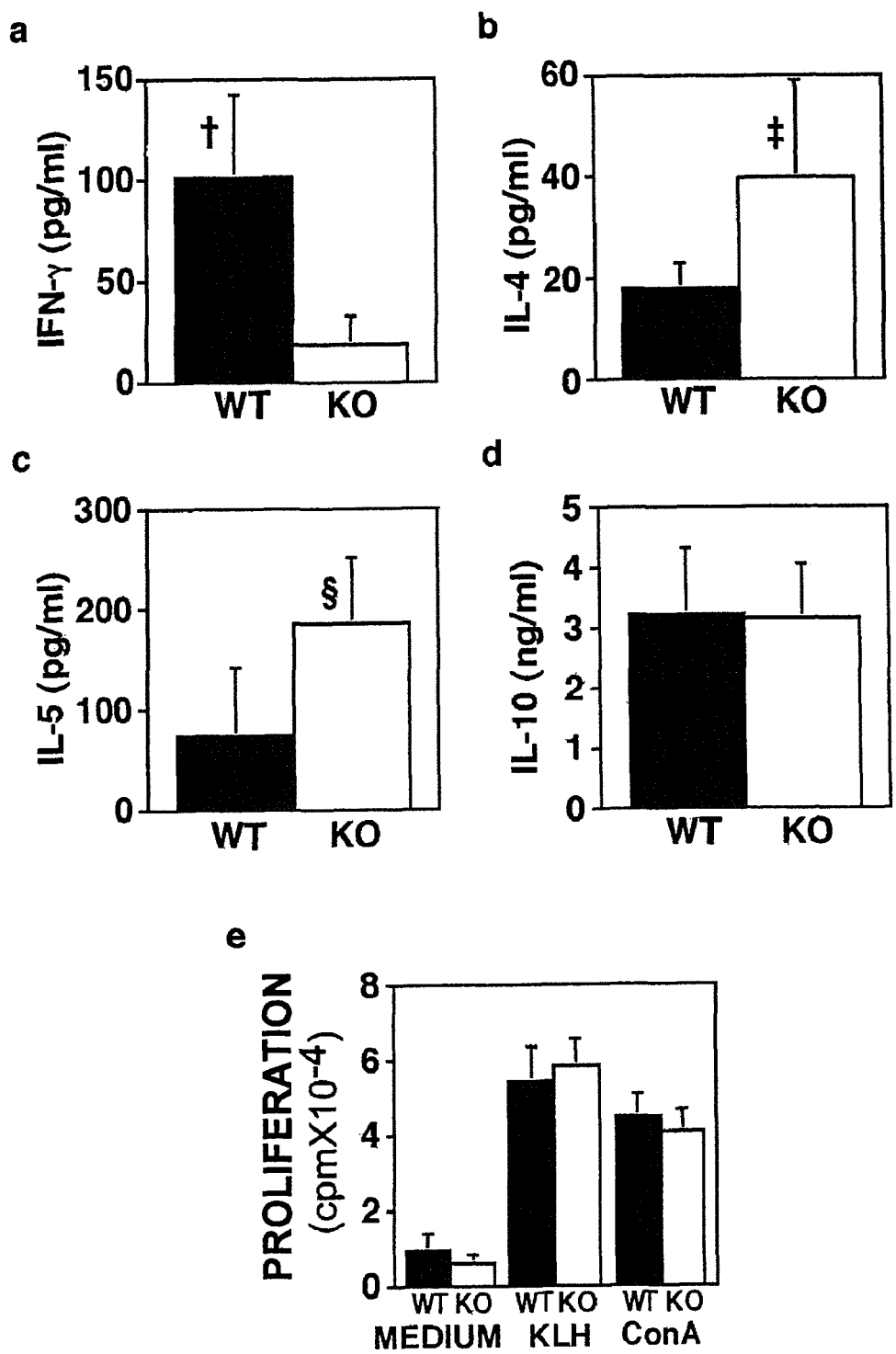

FIG. 4 shows graphs of antigen-induced cytokine production and proliferation by lymph nodes cells collected from SGRF/IL-23$^{-/-}$ and wild type mice. Groups of five mice (male, ten weeks old), were each immunized with KLH (200 μg) in CFA. Lymph nodes were harvested five days later, cultured for 48 hours in 300 μg/ml KLH, and then analyzed for their ability to produce IFN-γ (a), IL-4 (b), IL-5 (c), or IL-10 (d), or to proliferate (e). ConcanavalinA (ConA, 2 μg/ml) was used as the control for non-specific proliferation. Data are presented as the mean±SD values derived from the five mice in each group.

†, P<0.003; ‡, p<0.05; and §, p<0.03 (comparison between SGRF/IL-23$^{-/-}$ and wild type mice by unpaired t-test).

Figure 5:
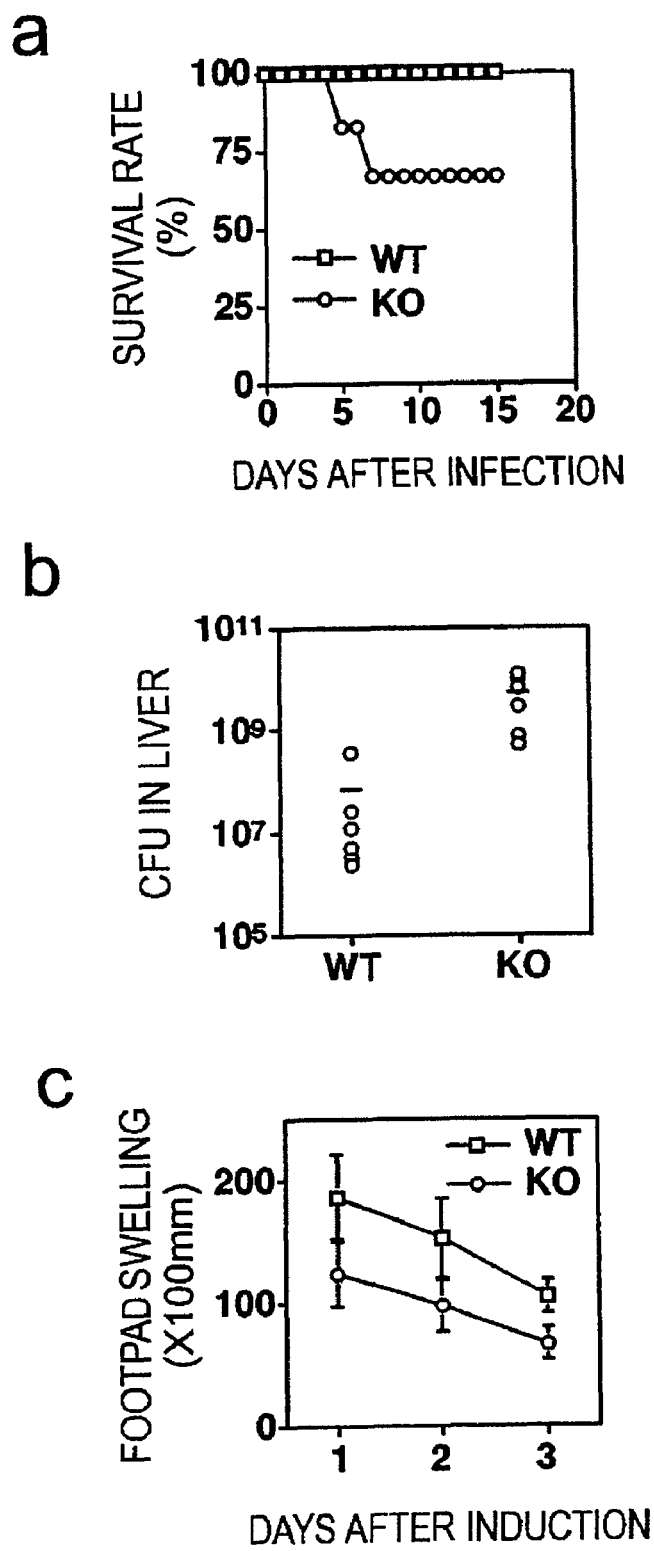

FIG. 5 depicts graphs representing susceptibility to *L. monocytogenes* infection, and DTH reactions, in wild type and SGRF/IL-23$^{-/-}$ mice.

a. Survival of SGRF/IL-23$^{-/-}$ or wild type mice after infection with *L. monocytogenes*. Groups of six mice (female, ten weeks old) were intravenously injected with 2.3×10$^6$ CFU of *L. monocytogenes*.

b. Multiplication of *L. monocytogenes* in SGRF/IL-23$^{-/-}$ or wild type mice. Four days after infection (3.1×10$^6$ CFU), livers were collected and bacteria number determined. The Mann-Whitney rank-test was used for statistical analysis (P<0.004).

c. Delayed-type hypersensitivity (DTH) reaction in SGRF/IL-23$^{-/-}$ and wild type mice. Six mice (male, ten weeks old) were subcutaneously immunized with 50 μl of CFA solution comprising mBSA (2.5 mg/ml). After five days, one rear footpad of each mouse was injected with 30 μl of 5 mg/ml mBSA. SGRF/IL-23$^{-/-}$ and wild type mice were compared at each time point using unpaired t-tests (P<0.007).

FIG. 6 depicts a graph and a photograph representing the result of EAE induction in wild type and SGRF/IL-23$^{-/-}$ mice. Mice (female, eight weeks old) were immunized with MOG peptide 35-55 in CFA, and subcutaneously injected with pertussis toxin according to the protocol for EAE induction.

a. A graph showing the clinical course of average disease scores in wild type mice (n=6) and SGRF/IL-23$^{-/-}$ mice (n=6). The scores of four of six wild mice that died are included in the graph throughout the experiment. The remaining mice survived.

b to e. Photographs representing histological sections of CNS from wild type and SGRF/IL-23$^{-/-}$ mice in which EAE was experimentally induced (b,d: wild type mice; c,e: SGRF/IL-23$^{-/-}$ mice). Sections were recovered one month after the mice were sensitized. Tissue sections (4 to 6 μm thick) were stained with hematoxylin and eosin (×200) (FIGS. 6b and 6c) or with Kluver-Barrera (×200) (FIGS. 6d and 6e). The arrows show infiltration of lymphocytes and the arrowhead shows demyelination.

BEST MODE FOR CARRYING OUT THE INVENTION

The present invention will be described below in detail with reference to Examples, but it is not to be construed as being limited thereto.

EXAMPLE 1

Expression Analysis of SGRF mRNA

Expression analysis of SGRF mRNA in mouse tissue was performed by Northern blotting using SGRF cDNA as a probe. High expression of mouse SGRF mRNA was confirmed in the thymus, and expression was detected in the brain and testis (FIG. 3a). RT-PCR analysis also detected mRNA expression in the spleen and lymph nodes (data not shown).

EXAMPLE 2

Construction of the Mice

Cloning of the SGRF gene was performed according to the method described in Patent EP1072610. The mouse SGRF genome was screened by Genome Systems, Inc. (now Incyte Genomics, Ins. St. Louis, USA). Two BAC (Bacteria Artificial Chromosome) clones were obtained. The Clone Addresses and GS Control Numbers identified by Genome System, Inc. are as follows:

| Clone Address | GS Control Number |
| --- | --- |
| 225(L12) | 24057 |
| 198(A03) | 24058 |

A large number of BAC clones were produced by known methods, and BAC DNAs were prepared using a Large-Construction Kit (QIAGEN).

Restriction digest mapping suggested that these BAC clones were identical to each other. However, a ~13 Kbp Hind III fragment was produced by digesting the GS Control Number 24057 clone, and a ~9 Kbp Bgl II fragment was produced by digesting the GS Control Number 24058 clone. The ~13 Kbp fragment was subcloned into pBluescript vector (STRATAGENE) at the Hind III site, and the ~9 Kbp fragment was cloned into a pGEM-T-easy vector (Promega) at the EcoRV site (converted to Bgl II). Vectors carrying each DNA fragment were referred to as pBSK-mSGRF (Hind III) and pGEM-mSGRF (Bgl II) respectively. The genomic sequence encoding the mouse SGRF (mSGRF) gene was determined using sequence analysis and is shown in FIGS. 1 and 2, and in SEQ ID NOs: 1 to 7 (note this sequence is that of 129/SV JII mice).

The above-mentioned sequence data results revealed that both the mouse SGRF (mSGRF) gene and the human SGRF (hSGRF) gene (GenBank Accession No. AB030001) comprise four exons. Therefore, a genetically modified mouse of the present invention can be constructed as follows: A targeting vector is constructed by replacing the SGRF exon region with an appropriate drug marker gene. The targeting vector is then transfected into mouse ES cell strains using electroporation or the like, and cell strains that undergo homologous recombination are selected. Specifically, this was performed as follows:

The mouse SGRF DNA fragment inserted into pGEM-mS-GRF (Bgl II) contained a ~9 Kbp promoter region, which included a region from the Bgl II site 18 bases upstream of the start codon to the Bgl II site located further upstream. pBSK-mSGRF (Hind III) also contained a DNA fragment that included a region from ~1.7 Kbp of the start codon to 13 Kbp downstream. The ~1.1 Kbp region between Intron 2 and Exon 4 (sequence data: from 5'-CTAAGCCGATGTTGATGT-GTC-3' (SEQ ID NO: 8) to 5'-GCAGATGCACAGTACTC-CAGACAGC-3' (SEQ ID NO:9)) was amplified by PCR using pBSK-mSGRF (Hind II) as a template, and the primers described below (FmSGREX2 and RSGR-A), which were designed to create restriction sites (Sal I, Pst I, and Xba I). The PCR product was then TA-cloned into a pGEM-T-Easy vector, and the vector was digested using Sal I and Xho I.

Forward Primer:

FmSGREX2: 5'-GTC GAC TGC AGT CTA GAC TAA GCC GAT GTT GAT GTG TC-3' (SEQ ID NO: 10)

Reverse Primer:

RSGR-A: 5'-GCT GTC TGG AGT ACT GTG CAT CTG C-3' (SEQ ID NO 11)

In this case, a knockout vector was constructed using a ~0.9 Kbp fragment (produced by digestion at Sal I and Xho I sites in the FmSGRFEX2 primer and in Exon 4 of the SGRF gene), and the above-described ~9 Kbp fragment of the mSGRF promoter region inserted into pGEM-mSGRF (Bgl II). Cell strains which did not undergo homologous recombination were eliminated by inserting a drug resistance gene (neo) between these fragments, and by adding a diphtheria toxin A fragment (DT-A).

Figure 3:
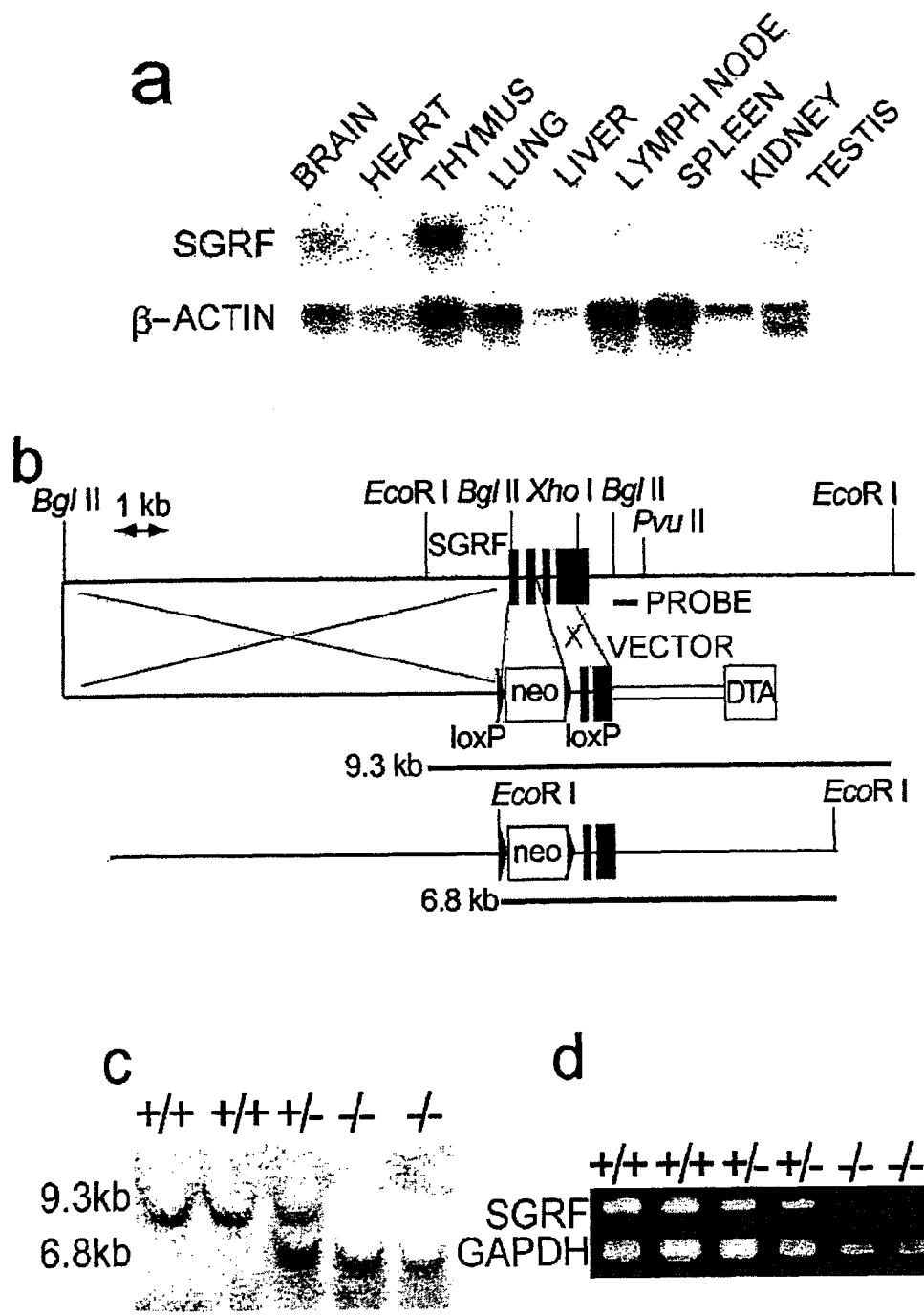
FIG. 3 depicts a photograph and a drawing, showing SGRF mRNA expression analysis in mouse tissue and the construction of SGRF/IL-23$^{-/-}$ mice.

In this Example, as described above, the SGRF gene was inactivated by replacing Exon 1 and 2 of the SGRF gene with a drug resistance gene (neo) (FIG. 3 (A)). Since this drug resistance gene (neo) would probably influence the expression of neighboring genes, a loxP sequence (5'-ATA ACT TCG TAT AGC ATA CAT TAT ACG AAG TTA T-3' (SEQ ID NO: 12)) was inserted at either side of the neo sequence. Thus, the neo can be deleted using a Cre protein, if a known or unknown gene be located near the SGRF gene. The targeting vector was digested at a single site using a restriction enzyme (Not I), and then transfected into ES cells by electroporation.

Homologous recombinants were constructed by transfecting AB2.2 cells (ES cells derived from 129SvEv mice) according to the manual attached to The Mouse Kit (Lexicon Genetics Inc.), commercially available from TAKARA. Homologous recombinants were selected by G418. PCR was used to screen for recombinants. ES cells used for screening were cultured in a 96-well plate. Each well was washed twice with 200 µl PBS and treated with cell lysis buffer (5 µl 10× LA buffer (use for TAKARA LA Taq), 5 µl 5% NP-40, 4 µl proteinase K (TAKARA, 20 mg/l), 35 µl distilled water) for two hours at 55 degrees Celsius. These cells were incubated at 95 degrees C. for 15 minutes to inactivate proteinase K, and then used for PCR samples. The PCR reaction mixture contained 1 µl of an above-mentioned PCR sample, 5 µl 10× LA buffer, 5 µl $MgCl_2$ (25 mM), 8 µl DNTP (2.5 mM), 0.4 µl each primers (50 µM each), 0.5 µl LA taq (TAKARA), and 29.7 µl distilled water (total 50 µl). PCR was performed under the following condition: preheating at 95 degrees C. for one minute; 35 cycles of amplification at 95 degrees C. for 30 seconds, 64 degrees C. for 30 seconds, and 72 degrees C. for 80 seconds; and heat extension at 72 degrees C. for seven minutes.

The primers were as below. A ~1.3 Kbp band was amplified in ES cell samples in which homologous recombination occurred. Primer Fneo-1 was in the drug resistance gene in the knockout vector, and primer RSFR-A was in Exon 4 of the SGRF gene, which was located outside of the knockout vector.

Reverse Primer:

RSGR-A: 5'-GCT GTC TGG AGT ACT GTG CAT CTG C-3' (SEQ ID NO: 13)

Forward Primer:

FNeo-1: 5'-CCG TGA TAT TGC TGA AGA GCT TGG C-3' (SEQ ID NO: 14)

420 and 760 ES cell clones were analyzed in the two experiments. Of these, two and six clones respectively were homologous recombinants. Thus the recombination efficiencies were 2/420 (0.467%) and 6/760 (0.79%), and the combined total recombination efficiency for both experiments was 0.68%.

Chimeric mice were obtained by injecting seven ES cell strains, in which one SGRF gene allele was inactivated, into blastocysts derived from C57BL/6J mice. Mice comprising cells in which one SGRF gene allele was inactivated (hereafter referred to as "SGRF/IL-23$^{+/-}$ mice") were obtained by mating C57BL/6 mice with the above-described chimeric mice. SGRF/IL-23$^{+/-}$ mice were obtained in four strains, clone numbers 11, 23, 75, and 86, of the seven cell strains used for the experiment. Mice derived from clone 11 and clone 86 were used for further studies. Mice in which both SGRF gene alleles were inactivated (hereafter referred to as "SGRF/IL-23$^{-/-}$ mice") were obtained by mating the SGRF/IL-23$^{+/-}$ mice with each other. Southern blot analysis was used to confirm the insertion of the mutant gene into one or both SGRF gene alleles in mice thus obtained (FIG. 3 (c)).

Loss of gene expression was confirmed by a reverse transcriptase polymerase chain reaction (RT-PCR) using thymus-derived polyA$^+$ RNA (FIG. 3 (d)). Both heterologous and homologous SGRF/IL-23 mice showed normal growth and appearance, and were able to reproduce.

EXAMPLE 3

Analysis of SGRF Gene-Deleted Mice (1) Cytokine Production in SGRF/IL-23$^{-/-}$ Mice Immunized with KLH The ability of lymph node cells, obtained from keyhole limpet haemocyanin (KLH)-immunized wild type mice (normal mice, SGRF/IL-23$^{+/+}$) and SGRF/IL-23$^{-/-}$ mice, to produce cytokines and to proliferate was examined in order to investigate the involvement of SGRF/IL-23 in antigen-induced cytokine production and ability to proliferate T cells.

To induce a Th1 response, mice were immunized subcutaneously at the base of their tail using 200 µg KLH in PBS, in a 1:1 emulsion with complete Freund's adjuvant (CFA), containing 5 mg/ml *Mycobacterium tuberculosis* strain H37Ra, (Difco Laboratories). After five days, inguinal lymph nodes were removed and the cells were cultured in RPMI1640 supplemented with 106 FCS and 0.3 mg/ml of KLH. To measure cytokine production, lymph node cells were cultured in 1 ml of medium in 24-well plates until the cells proliferated to 6×10$^6$ cells/ml. After culturing for 48 hours, culture supernatants were harvested and cytokine levels were determined using enzyme-linked immunosorbent assay (ELISA) kits, obtained from R&D Systems, according to the manufacturer's instructions. Furthermore, radiolabel incorporation into DNA was measured by MicroBeta scintillation counting (Perkin Elmer) as follows: After 48 hours of incubation, 0.25 µCi of [$^3$H]thymidine (Amersham Pharmacia) was added and incubated for four hours in 96-well flat-bottomed microplates in which there were $6\times10^6$ cells/ml in a total volume of 200 µl. Then, the degree of proliferation was measured.

IFN-γ production by SGRF/IL-23-deficient lymphocytes was significantly impaired compared to the production by wild-type lymphocytes (FIG. 4a), whereas KLH-induced IL-4 and IL-5 production was markedly enhanced (FIG. 4b,c). In contrast, both IL-10 production and KLH-induced proliferation were similar for wild type and SGRF/IL-23-deficient lymphocytes (FIG. 4d,e).

These data indicate that in SGRF/IL-23$^{-/-}$ mice, production of Th1-type cytokines is reduced, and production of Th2-type cytokines is increased.

(2) Defending the Body Against Pathogenic Microbes and DTH

Th1-type responses are important in defenses against intracellular pathogens such as *Listeria*, and Th1-type cytokines such as IFN-γ and TNF-α are essential for this defense (Kaufmann S H. Immunity to intracellular bacteria. Annu. Rev Immunol 11, 129-163 (1993)).

The survival rate of SGRF/IL-23$^{-/-}$ mice after *Listeria* infection, and the number of *Listeria* present in the liver four days after *Listeria* infection, were investigated to examine the involvement of SGRF/IL-23 in biophylaxis against pathogenic microbe infection.

Specifically, *Listeria* (serum type 4b) ($2.3\times10^6$ CFU/mouse) were injected intravenously (Suzuki H. et al., A role for macrophage scavenger receptors in atherosclerosis and susceptibility to infection. Nature 386, 292-296 (1997)) into either SGRF genotypic mice (male, ten weeks old) or wild type mice (male, ten weeks old) and the post-infection survival rates of the mice were examined everyday for 15 days. The results indicated the survival rate of SGRF/IL-23$^{-/-}$ mice was lower than that of wild type mice (FIG. 5a).

*Listeria* ($3.1\times10^6$ CFU/mouse) was also injected into mice in order to examine post-infection *Listeria* proliferation. Four days after infection, and under sterile conditions, the mice livers were removed and homogenized in sterile PBS. The homogenized tissues were diluted stepwise with PBS, plated on brain-heart infusion agar (Difco), and incubated at 37 degrees C. for 16 hours. CFUs were then counted. *L. monocytogenes* proliferation in the livers of SGRF/IL-23$^{-/-}$ mice four days after injection was significantly increased compared with that of wild-type mice (FIG. 5).

These results suggest that SGRF/IL-23$^{-/-}$ mice, compared with wild type mice, are susceptible (less resistant) to *L. monocytogenes*. Thus, these results suggest that SGRF/IL-23, as well as IL-12, contributes to the elimination of *L. monocytogenes*.

To further examine the role of SGRF/IL-23 on Th1-type immune responses, the present inventors investigated delayed-type hypersensitivity (DTH), which is the typical in vivo manifestation of cell-mediated immunity.

Delayed-type hypersensitivity was induced by using a well known method (Immunity, Vol. 4, p 471 (1996)). Specifically, mice were immunized with methyl BSA (SIGMA) by intradermal injection of a 50 µl emulsion of 2.5 mg/ml mBSA in CFA (Beckton Dickinson) at two sites on the abdomen. Five days after immunization, DTH was induced in the mice by subcutaneous injection of 30 µl of 5.0 mg/ml mBSA into one rear footpad. A comparable volume of PBS was injected into the other rear footpad as a control. Measurements of footpad swelling were taken using a micrometer (Ozaki Inc.) at 24, 48 and 72 hours after injection. Footpad swelling following methyl BSA injection was measured by comparison with that caused by PBS injection, and average values for each group were obtained (n=6).

The results showed that for three days after injection, specific footpad swelling was suppressed in the SGRF/IL-23$^{-/-}$ mice (FIG. 5c).

These results indicate that SGRF/IL-23 plays an important role in Th1-type responses. Therefore, it is predicted that SGRF is a factor necessary for the defense against infections caused by pathogenic microbes.

(3) Involvement in Autoimmune Disease Development

The involvement of SGRF/IL-23 in autoimmune diseases such as multiple sclerosis, chronic rheumatoid arthritis, and autoimmune colitis can be investigated by inducing disease models in the genetically modified mice of the present invention according to known immunological methods, and then making comparisons with normal mice.

Experimental autoimmune encephalomyelitis (EAE) is a central nervous system (CNS) autoimmune disease mediated by Th1 responses, and is known as a model for human multiple sclerosis. The following experiment was performed to investigate the role of SGRF/IL-23 in autoimmune disease.

EAE was induced in SGRF/IL-23$^{-/-}$ mice and wild type mice by well known methods (J. Exp. Med. Vol. 186 p 1233, 1997). Specifically, 300 µg of MOG peptide (MEV GWY RSP FSR VVH LYR NGK/SEQ ID NO: 15; Sawady Technology) and 0.2 ml of CFA (including 500 µg of *Mycobacterium tuberculosis* strain H37Ra (Difco Laboratories)) was injected subcutaneously into one side of the mice abdomens on day 0 and day 7. 200 ng of Pertussis toxin (List Biological Laboratories) was injected into the mice veins on day 0, and administrated intraperitoneally two days after the first immunization.

After inducing EAE in the mice, pathology scoring was conducted according to a known method, and using a scale from 1 to 5: 1, normal; 2, wobbly gait; 3, hind limb paralysis; 4, hind and fore limb paralysis; 5, death. Each mouse was scored and average values were collected. The results indicated that SGRF/IL-23$^{-/-}$ mice showed significant resistance to MOG-induced EAE compared to wild type mice. Six SGRF/IL-23$^{-/-}$ mice and six wild type mice were used for the experiment in FIG. 6. Although EAE developed in two of the six SGRF/IL-23$^{-/-}$ mice, their pathology scores were low. On the other hand, all wild type mice developed severe EAE, and four of the six wild type mice died.

Histological analysis was performed on EAE-induced SGRF/IL-23$^{-/-}$ mice and wild type mice. Spinal cords from EAE-induced mice were removed and fixed with 20% formalin neutral buffered solution (Wako) in order to conduct histological analysis. Paraffin sections were prepared and stained using hematoxylin/eosin and Kluver-Barrera staining in the Sapporo General Pathology Co. Ltd.

Histological analysis of the spinal cords of wild-type mice injected with MOG peptide showed typical lymphocyte infiltration (FIG. 6b) and demyelination (FIG. 6d). In contrast, no histological change was observed in the spinal cords of SGRF/IL-23$^{-/-}$ mice (FIG. 6c, e).

These results indicate that SGRF/IL-23$^{-/-}$ is an important component in the development of EAE, and that SGRF could be a new target for multiple sclerosis (MS) therapy in humans.

(4) Involvement in the Bone Metabolism

The well known OVX model, in which ovaries are removed from a female mouse, can be used to determine whether SGRF is involved in the bone metabolism.

INDUSTRIAL APPLICATION

The present invention provides genetically modified animals in which both SGRF gene alleles are inactivated and SGRF activity has been eliminated. The genetically modified animals and ES cells of the present invention can be used to predict the side effects of SGRF inhibitors such as anti-SGRF antibodies or SGRF antagonists. The genetically modified animals and ES cells of the present invention can also be used to determine whether a test protein or small molecule comprises the function of substituting for SGRF function, or whether it can be used to screen for DNA that encodes a protein comprising the function of substituting for SGRF function.

Furthermore, since the genetically modified mice (SGRF KO mouse) are susceptible to infection by the pathogenic microbe *Listeria*, SGRF or alternative substances involved in SGRF signaling are considered to be therapeutic agents against pathogenic microbes.

Moreover, experimental autoimmune encephalomyelitis is not easily induced in SGRF KO mice and delayed-hypersensitivity is reduced. Therefore, antagonists that inhibit SGRF function are considered to be strong candidates for therapeutic agents for autoimmune or inflammatory diseases.

The invention claimed is:

1. A knockout mouse whose genome comprises mutations in both alleles of the mouse's endogenous Interleukin-Six, G-CSF Related Factor (SGRF)/Interleukin-23 (IL-23) gene, wherein said mouse lacks functional SGRF and exhibits, as compared to a wild type mouse, at least one of: (a) increased resistance to experimental autoimmune encephalitis (EAE); (b) increased resistance to delayed-type hypersensitivity (DTH); and (c) increased susceptibility to infection by an intracellular pathogenic microbe.

2. A method for producing an anti-SGRF antibody, the method comprising injecting the knockout mouse of claim 1 with a SGRF peptide, such that the mouse produces the anti-SGRF antibody.

3. The knockout mouse of claim 1, wherein said mutations are in one or more exons of the SGRF/IL-23 alleles.

4. The knockout mouse of claim 1, wherein said mutations are in a promoter region of the SGRF/IL-23 alleles.

5. The knockout mouse of claim 1, wherein said mutations are insertions of a foreign gene.

6. The knockout mouse of claim 1, wherein said mutations are partial deletions of the SGRF/IL-23 alleles.

7. A method of screening, the method comprising:
(a) administering a test compound to the knockout mouse of claim 1;
(b) determining the knockout mouse's susceptibility to at least one of: EAE, DTH, and infection by an intracellular pathogenic microbe; and
(c) selecting the compound if the compound has at least one of the following effects: decreasing the knockout mouse's resistance to EAE, decreasing the knockout mouse's resistance to DTH, and decreasing the knockout mouse's susceptibility to infection by an intracellular pathogenic microbe.

8. A method of screening, the method comprising:
(a) administering a test compound to the knockout mouse of claim 3;
(b) determining the knockout mouse's susceptibility to at least one of: EAE, DTH, and infection by an intracellular pathogenic microbe; and
(c) selecting the compound if the compound has at least one of the following effects: decreasing the knockout mouse's resistance to EAE, decreasing the knockout mouse's resistance to DTH, and decreasing the knockout mouse's susceptibility to infection by an intracellular pathogenic microbe.

9. A method of screening, the method comprising:
(a) administering a test compound to the knockout mouse of claim 4;
(b) determining the knockout mouse's susceptibility to at least one of: EAE, DTH, and infection by an intracellular pathogenic microbe; and
(c) selecting the compound if the compound has at least one of the following effects: decreasing the knockout mouse's resistance to EAE, decreasing the knockout mouse's resistance to DTH, and decreasing the knockout mouse's susceptibility to infection by an intracellular pathogenic microbe.

10. A method of screening, the method comprising:
(a) administering a test compound to the knockout mouse of claim 5;
(b) determining the knockout mouse's susceptibility to at least one of: EAE, DTH, and infection by an intracellular pathogenic microbe; and
(c) selecting the compound if the compound has at least one of the following effects: decreasing the knockout mouse's resistance to EAE, decreasing the knockout mouse's resistance to DTH, and decreasing the knockout mouse's susceptibility to infection by an intracellular pathogenic microbe.

11. A method of screening, the method comprising:
(a) administering a test compound to the knockout mouse of claim 6;
(b) determining the knockout mouse's susceptibility to at least one of: EAE, DTH, and infection by an intracellular pathogenic microbe; and
(c) selecting the compound if the compound has at least one of the following effects: decreasing the knockout mouse's resistance to EAE, decreasing the knockout mouse's resistance to DTH, and decreasing the knockout mouse's susceptibility to infection by an intracellular pathogenic microbe.

* * * * *